United States Patent
Weismantel et al.

(10) Patent No.: US 8,575,389 B2
(45) Date of Patent: Nov. 5, 2013

(54) NEUTRALIZATION PROCESS

(75) Inventors: Matthias Weismantel, Jossgrund-Oberndorf (DE); Michael de Marco, Weinheim (DE); Dominicus van Esbroeck, Nanjing (CN); Karl J. Possemiers, Gravenwezel (BE); Ronny De Kaey, Mortsel (BE)

(73) Assignee: BASF SE, Ludwigshafen (DE)

( * ) Notice: Subject to any disclaimer, the term of this patent is extended or adjusted under 35 U.S.C. 154(b) by 591 days.

(21) Appl. No.: 12/065,056

(22) PCT Filed: Aug. 31, 2006

(86) PCT No.: PCT/EP2006/065849
§ 371 (c)(1),
(2), (4) Date: Feb. 27, 2008

(87) PCT Pub. No.: WO2007/028751
PCT Pub. Date: Mar. 15, 2007

(65) Prior Publication Data
US 2008/0194863 A1    Aug. 14, 2008

(30) Foreign Application Priority Data
Sep. 7, 2005 (DE) .......................... 10 2005 042 604

(51) Int. Cl.
*C07C 51/42*    (2006.01)
(52) U.S. Cl.
USPC ........... 562/600; 562/400; 562/512; 562/534; 562/538; 562/547
(58) Field of Classification Search
USPC .......... 562/400, 512, 534, 538, 545–547, 600
See application file for complete search history.

(56) References Cited

U.S. PATENT DOCUMENTS

| | | | |
|---|---|---|---|
| 5,210,298 A * | 5/1993 | Shimomura et al. | 562/598 |
| 6,710,141 B1 | 3/2004 | Heide et al. | |
| 6,727,345 B2 | 4/2004 | Kajikawa et al. | |
| 6,911,499 B1 | 6/2005 | Brehm et al. | |
| 7,157,598 B2 | 1/2007 | Fuchs et al. | |
| 2003/0020199 A1 | 1/2003 | Kajikawa et al. | |
| 2005/0096445 A1* | 5/2005 | Fuchs et al. | 526/317.1 |

FOREIGN PATENT DOCUMENTS

| | | |
|---|---|---|
| DE | 34 32 082 | 3/1986 |
| EP | 0 372 706 | 6/1990 |
| EP | 0 574 260 | 12/1993 |
| EP | 1 470 905 | 10/2004 |
| WO | WO-01/16197 | 3/2001 |
| WO | WO-01/38402 | 5/2001 |
| WO | WO-03/004237 | 1/2003 |
| WO | WO-03/022896 | 3/2003 |
| WO | WO-03/051415 | 6/2003 |
| WO | WO-03/095410 | 11/2003 |

OTHER PUBLICATIONS

Ullmann et al., *Ullmann's Encyclopedia of Industrial Chemistry*, 6th ed., vol. 35, pp. 1-21, New York: Wiley, 2005.
International Search Report in PCT/EP2006/065849 dated Feb. 4, 2007.

* cited by examiner

*Primary Examiner* — Sudhakar Katakam
(74) *Attorney, Agent, or Firm* — Marshall, Gerstein & Borun LLP

(57) ABSTRACT

The invention relates to a continuous neutralization process in which at least one ethylenically unsaturated carboxylic acid is neutralized at least partly with a base and the temperature of the neutralized solution is less than 70° C., and also to an apparatus for carrying out the process.

15 Claims, 1 Drawing Sheet

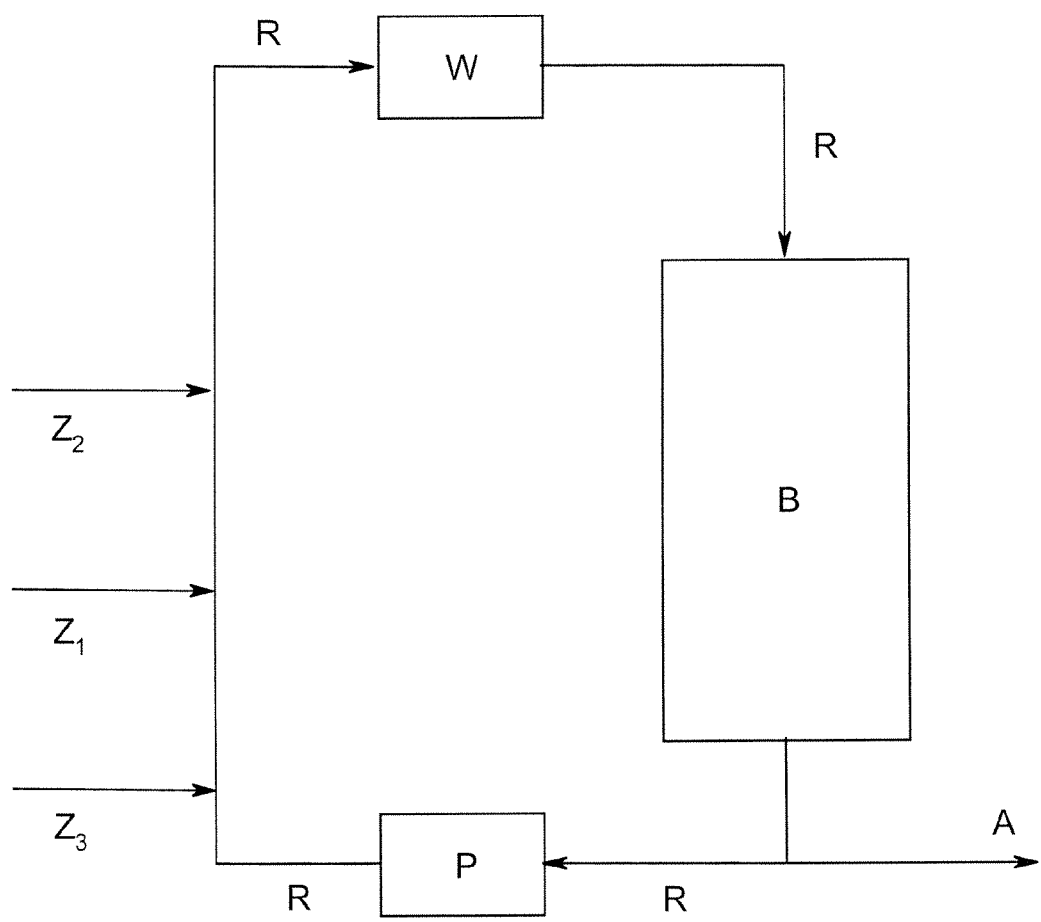

NEUTRALIZATION PROCESS

CROSS-REFERENCE TO RELATED APPLICATIONS

This is the U.S. national phase application of International Application No. PCT/EP2006/065849, filed Aug. 31, 2006, which claims the benefit of German patent application No. 10 2005 042 604.2, filed Sep. 7, 2005.

The present invention relates to a continuous neutralization process for ethylenically unsaturated carboxylic acids and to an apparatus for carrying out the process.

Further embodiments of the present invention can be taken from the claims, the description and the examples. It is evident that the features of the inventive subject matter which have been mentioned above and are yet to be explained below are usable not only in the combination specified in each case but also in other combinations without leaving the scope of the invention.

Water-absorbing polymers are especially polymers of (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, preference being given to water-absorbing polymers based on partly neutralized acrylic acid. Such polymers are used as products that absorb aqueous solutions to produce diapers, tampons, sanitary napkins and other hygiene articles, but also as water-retaining agents in market gardening.

The preparation of the water-absorbing polymers is described, for example, in the monograph "Modern Superabsorbent Polymer Technology", F. L. Buchholz and A. T. Graham, Wiley-VCH, 1998, or in Ullmann's Encyclopedia of Industrial Chemistry, 6th Edition, Volume 35, pages 73 to 103. The preferred preparation process is solution or gel polymerization. In this technology, a monomer mixture is firstly prepared and is neutralized batchwise and then transferred to a polymerization reactor, or initially charged actually within the polymerization reactor. In the batchwise or continuous process which follows, the reaction is effected to give the polymer gel which, in the case of a stirred polymerization, is already in comminuted form. The polymer gel is subsequently dried, ground and sieved and then transferred to further surface treatment.

A continuous polymerization process forms the basis, for example, of WO 01/38402, in which the aqueous monomer solution is fed continuously to a mixing kneader with at least two axially parallel-rotating shafts.

Continuous gel polymerizations are also known from WO 03/004237, WO 03/022896 and WO 01/016197.

Both in the continuous and in the batchwise polymerization, the acrylic acid is neutralized batchwise in the case of preneutralization. Typically, the reactants (acrylic acid, water, optional comonomers and sodium hydroxide solution) are metered in and mixed batchwise in the polymerization reactor in the case of solution polymerization. In this step, the remaining course of the polymerization and also the expected polymer properties are laid down to a very substantial extent. The degree of crosslinking of the base polymer and the degree of neutralization are typically determined in this step. The degree of neutralization of the monomers is between 0 and 80 mol %. In the case of acidic polymerization, the resulting polymer gel is typically neutralized afterward to an extent of from 50 to 80 mol %, preferably to an extent of from 60 to 75 mol %, by adding sodium hydroxide or sodium carbonate solution to the acidic polymer gel and incorporating it.

Neutralization processes are described, for example, in EP-A 0 372 706, EP-A 0 574 260, WO 03/051415 and EP-A 1 470 905.

EP-A 0 372 706 describes a three-stage neutralization process in which acrylic acid and sodium hydroxide solution are metered in simultaneously in a first stage in such a way that a degree of neutralization of from 75 to 100 mol % is maintained, the degree of neutralization is raised to from 100.1 to 110 mol % in a second stage in order to hydrolyze diacrylic acid present as an impurity in the acrylic acid used, and a degree of neutralization of from 20 to 100 mol % is established in a third stage by addition of further acrylic acid.

EP-A 0 574 260 discloses, on page 7, lines 38 to 41, that sodium hydroxide solution is advantageously initially charged in the neutralization and acrylic acid is subsequently added with cooling.

WO 03/051415 teaches a process for preparing water-absorbing polymers, in which the monomer solution has a minimum temperature of 40° C.

EP-A 1 470 905 describes, in the examples, the continuous neutralization of acrylic acid immediately upstream of the polymerization reactor. Owing to the heat of neutralization, the temperature rises to 95° C.

It is known that the reactivity of acrylic acid differs very greatly from that of its salts, which is why the course of the polymerization is also greatly dependent upon the pH at which it takes place. In a graphic illustration in the monograph "Modern Superabsorbent Polymer Technology", F. L. Buchholz and A. T. Graham, Wiley-VCH, 1998, or in Ullmann's Encyclopedia of Industrial Chemistry, 6th Edition, Volume 35, page 35, the polymerization rate is plotted as a function of the pH. According to this, the polymerization rate passes through a minimum at a pH of from 6 to 7. However, this corresponds to the pH which is generally desired in the saleable products. This behavior is explained by the occurrence of electrostatic repulsion reactions, which are not present in the case of very substantially undissociated acrylic acid, between the charged monomers in salt form and the growing free-radical chain, which leads to slowing of the reaction.

It is also known that unneutralized acrylic acid can be polymerized more easily than preneutralized systems. However, this difference is reduced in the case of rising monomer concentration, in particular because a higher monomer concentration suppresses the dissociation of the acrylic acid salts.

In order to take account of all of these details of the reaction mechanism, compromises are typically entered into in conducting the reaction.

Generally, the degree of neutralization of the acrylic acid is established actually before it enters the continuous polymerization. The neutralization is effected batchwise. Batchwise neutralization has the advantage that acrylic acid and/or sodium hydroxide solution can be metered in under temperature control. This prevents overheating and undesired polymerization in the mixture vessel. The degree of neutralization is selected in accordance with the polymerization conditions and the desired absorption profile and, if desired, corrected in a subsequent neutralization which is usually effected on the polymer gel.

A particular disadvantage of neutralization as a preceding batchwise process step is the logistical demands. The provision of reservoir tanks, vessels or containers which store the partly neutralized acrylic acid, and also the complete apparatus demands have a disadvantageous effect on the economic viability of the process.

It would therefore be desirable to carry out the neutralization continuously. Continuous neutralization could then be combined advantageously with a continuous polymerization, in which case the logistical demands and the provision of reservoir vessels is minimized. However, continuous neutralization is found to be problematic owing to the evolution of heat which occurs, since this results in undesired premature polymerization. In all cases, the further course of the continuous polymerization is adversely effected by polymer gel which has already formed, especially as a result of blockages in lines which have only been designed for liquid transport.

It was an object of the present invention to provide a continuous neutralization process in which the occurrence of undesirably high temperature peaks can be avoided.

The object is achieved by a neutralization process in which at least one ethylenically unsaturated carboxylic acid is neutralized at least partly with a base, which comprises carrying out the neutralization continuously and the temperature of the neutralized solution being less than 70° C.

Preference is given to using ethylenically unsaturated carboxylic acids such as acrylic acid, methacrylic acid, maleic acid, fumaric acid and itaconic acid. Acrylic acid is particularly preferred.

The temperature of the ethylenically unsaturated carboxylic acid is typically from 0 to 40° C., preferably from 5 to 35° C., more preferably from 10 to 30° C., most preferably from 15 to 25° C., while ensuring sufficient distance from melting point. In the case of use of acrylic acid, the temperature should not go below 15° C. in any case.

A preferred base is aqueous alkali. Aqueous alkali is all aqueous solutions with an alkaline reaction, i.e. aqueous solutions with a pH of at least 8, preferably at least 10, more preferably at least 12, most preferably at least 14.

The alkaline salts usable in the aqueous neutralizing agent are preferably alkali metal hydroxides, alkali metal oxides, alkali metal carbonates and alkali metal hydrogencarbonates and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate and mixtures thereof. Typically, the alkali content in the aqueous alkali is at least 10% by weight, preferably at least 20% by weight, more preferably at least 30% by weight, most preferably at least 40% by weight.

The temperature of the aqueous alkali is typically from 0 to 45° C., preferably from 5 to 40° C., more preferably from 10 to 35° C., most preferably from 15 to 30° C., while avoiding oversaturations and thus precipitations.

When the alkali content of the aqueous alkali is at least 25% by weight, higher temperatures are advantageous, typically of from 10 to 60° C., preferably of from 20 to 55° C., more preferably of from 30 to 50° C., most preferably of from 40 to 45° C.

The ratio of ethylenically unsaturated carboxylic acid to base is typically selected such that the degree of neutralization of the ethylenically unsaturated carboxylic acid, after neutralization, is preferably from 25 to 85 mol %, preferentially from 27 to 80 mol %, more preferably from 27 to 30 mol % or from 40 to 75 mol %.

The degree of neutralization is the molar ratio of neutralized ethylenically unsaturated carboxylic acid after neutralization to the total amount of ethylenically unsaturated carboxylic acid used before neutralization.

The neutralization is carried out continuously. This means that ethylenically unsaturated carboxylic acid and/or base are supplied to the neutralization region and neutralized solution is simultaneously withdrawn from the neutralization region. Of course, startup and shutdown operations of the continuous neutralization process are excluded from this.

The solution withdrawn continuously from the neutralization region is at least partly transferred continuously into the polymerization.

The polymerization is preferably likewise carried out continuously.

The neutralization region is the region in which the neutralization takes place to a substantial extent, i.e. the region in which ethylenically unsaturated acid and base react with salt formation (neutralization).

The neutralization has substantially been completed when the conversion of the neutralization is at least 90 mol %, preferably at least 95 mol %, more preferably at least 98 mol %, most preferably at least 99 mol %. The conversion can be determined easily via the heat of neutralization released by comparison with the theoretical exothermicity.

The continuous neutralization is carried out in such a way that the temperature of the neutralized solution is preferably less than 60° C., preferentially less than 50° C., more preferably less than 40° C., most preferably less than 30° C., the temperature being the average temperature after neutralization, i.e. the mean temperature after full exothermicity.

The neutralization process according to the invention is of course also suitable for preparing neutralized solutions with a temperature of 70° C. and more. However, the polymerization tendency of the solution rises with rising temperature.

The distance between neutralization and polymerization is typically at least 1 m, preferably at least 5 m, more preferably at least 10 m, most preferably at least 20 m, and typically not more than 100 m, the distance being the length of the route that the monomer solution passes through in passing directly between the alkali metering and polymerization reactor.

In addition, the neutralized solution may be diluted with water. The dilution with water allows the solids content of the neutralized solution to be adjusted. The solids content is the sum of the proportions by weight of neutralized ethylenically unsaturated carboxylic acid and, if desired, excess ethylenically unsaturated carboxylic acid or excess base. The solids content of the neutralized solution is typically from 10 to 80% by weight, preferably from 20 to 70% by weight, more preferably from 30 to 60% by weight.

The temperature of the water is typically from above 0 to 40° C., preferably from 5 to 35° C., more preferably from 10 to 30° C., most preferably from 15 to 25° C.

Advantageously, the neutralized solution is cooled, in which case the heat exchangers usable for cooling are not subject to any restriction. The neutralized solution is cooled to a temperature of preferably less than 50° C., preferentially less than 40° C., more preferably less than 30° C., most preferably less than 20° C. The cooling should be as close as possible to the neutralization, since high residence times of the neutralized solution at high temperatures can thus be avoided.

Preference is given to premixing water and base. In this case, the heat of dissolution released can be removed actually before the neutralization, for example by means of suitable heat exchangers.

In a particularly preferred embodiment of the present invention, a portion of the neutralized solution is recycled into the neutralization, preferably cooled.

The recycling allows the heat of neutralization and the heat of dissolution to be distributed better and temperature peaks (peak temperature) in the mixture to be kept low. The proportion of recycled neutralized solution is typically from 25 to 99%, preferably from 33 to 98%, more preferably from 50 to 95%, most preferably from 80 to 90%, based in each case on the neutralized solution.

The ethylenically unsaturated carboxylic acid, the base and, if desired, the water may be metered into the recycled neutralized solution at any point. Preference is given to metering in the liquids in succession, particular preference to metering in base and ethylenically unsaturated carboxylic acid in succession, very particular preference to metering in water, base and ethylenically unsaturated carboxylic acid in succession.

Advantageously, at least one of the reactants is metered in via two or more separate addition points.

For example, the reactants may be metered in via two, three, four, five or six addition points, the addition points preferably being arranged such that they have a common axis (for two addition points) or form a symmetrical star (for at least three addition points), and the axis or star is at right angles to the flow direction of the neutralized solution (multiple addition points).

The base is metered in particularly advantageously when two, three or four multiple addition points are arranged in succession.

The division into a plurality of addition points brings about more uniform mixing and lower temperature peaks, which reduces the risk of undesired polymerization.

In a further embodiment, water and base are metered in such that the water encloses the base on entry into the neutralization. To this end, for example, two tubes inserted into one another may be used, in which case the base is metered in through the inner tube and the water through the annular gap between inner and outer tube.

Advantageously, the neutralization comprises an additional vessel as a buffer vessel.

An exemplary inventive neutralization is shown by FIG. 1, the reference symbols having the following definitions:

| | |
|---|---|
| $Z_1$ to $Z_3$ | feeds for reactants 1 to 3 |
| A | outlet |
| B | vessel |
| P | pump |
| R | ring line |
| W | heat exchanger |

By means of a pump P, neutralized solution is recycled partly via the ring line R. The rest of the neutralized solution is sent via the outlet A to further use. The vessel B serves as a buffer. 50% by weight sodium hydroxide solution is preferably metered in via inlet $Z_1$, preferably acrylic acid via inlet $Z_2$ and preferably water via inlet $Z_3$.

In order that the reactants are mixed very intensively into the recycled neutralized solution, the flow at the point of mixing-in should be very turbulent. The mixing-in point is the place where the particular reactant meets the recycled neutralized solution.

In a preferred embodiment of the present invention, at least one of the reactants is metered into a Venturi tube; preferably, all reactants are metered into a Venturi tube; more preferably, all reactants are metered into a common Venturi tube.

A Venturi tube is a pipe constriction of a restricted length in which pressure drop is converted substantially reversibly to kinetic energy. To this end, the cross section $F_1$ is reduced to the cross section $F_2$ over the zone $L_1$, the cross section $F_2$ is kept constant over the zone $L_2$ and the cross section $F_2$ is widened again to the cross section $F_1$ over the zone $L_3$. The cross section $F_1$ is greater than the cross section $F_2$ and the length $L_3$ is greater than the length $L_1$.

The reactants for the neutralization are preferably metered in in the region of the zone $L_2$ with the cross section $F_2$.

The optimal design of a Venturi tube is known per se to those skilled in the art. The Venturi tube is preferably designed such that the pressure in the region of the zone $L_2$ is less than the ambient pressure (suction conveying) and/or that the flow in the region of the zone $L_2$ is turbulent, in which case the Reynolds number should be at least 1000, preferably at least 2000, more preferably at least 3000, most preferably at least 4000, and typically less than 10 000 000.

The inventive continuous neutralization process enables polymerization-sensitive ethylenically unsaturated acids to be neutralized in a particularly gentle manner. Local overheating which can induce undesired polymerization is reliably prevented.

The continuous neutralization process according to the invention is also suitable for batchwise polymerization processes. For example, the vessel B according to FIG. 1 can be used as a reservoir vessel for a batchwise polymerization. Compared to the conventional batchwise neutralization, the continuous neutralization process enables distinctly improved heat removal.

The present invention further provides a process for preparing water-absorbing polymers by using a neutralized solution prepared by the neutralization process according to the invention as the monomer solution.

Preference is given to combining the inventive continuous neutralization process with a continuous polymerization process, in which case preference is given to carrying out all process steps, such as neutralization, polymerization, drying, grinding, sieving, postcrosslinking and sieving, continuously.

The water-absorbing polymers are obtained, for example, by polymerization of a monomer solution comprising
a) at least one ethylenically unsaturated carboxylic acid,
b) at least one crosslinker,
c) if desired one or more ethylenically and/or allylically unsaturated monomers copolymerizable with the monomer a), and
d) if desired one or more water-soluble polymers onto which the monomers a), b) and if appropriate c) can be at least partly grafted.

Suitable ethylenically unsaturated carboxylic acids a) are, for example, acrylic acid, methacrylic acid, maleic acid, fumaric acid and itaconic acid. Particularly preferred monomers are acrylic acid and methacrylic acid. Very particular preference is given to acrylic acid.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol refers to compounds of the following formula:

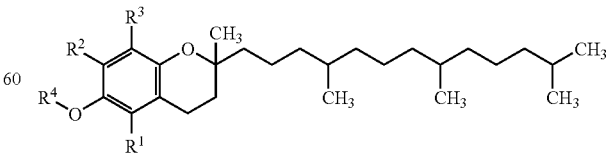

where $R^1$ is hydrogen or methyl, $R^2$ is hydrogen or methyl, $R^3$ is hydrogen or methyl and $R^4$ is hydrogen or an acyl radical having from 1 to 20 carbon atoms.

Preferred R⁴ radicals are acetyl, ascorbyl, succinyl, nicotinyl and other physiologically tolerable carboxylic acids. The carboxylic acids may be mono-, di- or tricarboxylic acids.

Preference is given to alpha-tocopherol where $R^1=R^2=R^3=$methyl, especially racemic alpha-tocopherol. $R^1$ is more preferably hydrogen or acetyl. Especially preferred is RRR-alpha-tocopherol.

The monomer solution comprises preferably not more than 130 ppm by weight, more preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having an appropriate hydroquinone monoether content.

The crosslinkers b) are compounds having at least two polymerizable groups which can be free-radically polymerized into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates, as described in EP-A 0 547 847, EP-A 0 559 476, EP-A 0 632 068, WO 93/21237, WO 03/104299, WO 03/104300, WO 03/104301 and DE-A 103 31 450, mixed acrylates which, as well as acrylate groups, comprise further ethylenically unsaturated groups, as described in DE-A 103 31 456 and WO 04/013064, or crosslinker mixtures as described, for example, in DE-A 195 43 368, DE-A 196 46 484, WO 90/15830 and WO 02/32962.

Suitable crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described, for example, in EP-A 0 343 427. Suitable crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. In the process of the invention, it is possible to use di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane.

Very particularly preferred crosslinkers b) are polyethoxylated and/or -propoxylated glycerols which have been esterified with acrylic acid or methacrylic acid to di- or triacrylates, as described, for example, in WO 03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 ppm by weight) in the water-absorbing polymer and the aqueous extracts of the water-absorbing polymers produced therewith have an almost unchanged surface tension (typically not less than 0.068 N/m) compared with water at the same temperature.

The amount of crosslinker b) is preferably from 0.01 to 1% by weight, more preferably from 0.05 to 0.5% by weight, most preferably from 0.1 to 0.3% by weight, based in each case on the monomer a).

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

For optimal action, the preferred polymerization inhibitors require dissolved oxygen. Typically, the monomer solutions are substantially freed of oxygen before the polymerization (inertization), for example by means of flowing an inert gas, preferably nitrogen, through them. This distinctly weakens the action of the polymerization inhibitors. The oxygen content of the monomer solution is preferably lowered to less than 1 ppm by weight and more preferably to less than 0.5 ppm by weight before the polymerization.

The preparation of a suitable base polymer and also further suitable hydrophilic ethylenically unsaturated monomers d) is described in DE-A 199 41 423, EP-A 0 686 650, WO 01/45758 and WO 03/104300.

Water-absorbing polymers are typically obtained by addition polymerization of an aqueous monomer solution and, if desired, subsequent comminution of the hydrogel. Suitable preparation methods are described in the literature. Water-absorbing polymers are obtainable, for example, by gel polymerization in a batch process or tubular reactor and subsequent comminution in a meat grinder, extruder or kneader (EP-A-0 445 619, DE-A-198 46 413)

addition polymerization in a kneader with continuous comminution by contrarotatory stirring shafts for example (WO 01/38402)

addition polymerization on a belt and subsequent comminution in a meat grinder, extruder or kneader (DE-A-38 25 366, U.S. Pat. No. 6,241,928)

emulsion polymerization, which produces bead polymers having a relatively narrow gel size distribution (EP-A-0 457 660)

in situ addition polymerization of a woven fabric layer which, usually in a continuous operation, has previously been sprayed with aqueous monomer solution and subsequently been subjected to a photopolymerization (WO 02/94328, WO 02/94329).

The reaction is preferably carried out in a kneader as described for example in WO 01/38402, or on a belt reactor as described for example in EP-A 0 955 086.

Neutralization can also be carried out partly after the polymerization, at the hydrogel stage. It is therefore possible to neutralize up to 40 mol %, preferably from 10 to 30 mol % and more preferably from 15 to 25 mol % of the acid groups before the polymerization by adding a portion of the neutralizing agent to the monomer solution and setting the desired final degree of neutralization only after the polymerization, at the hydrogel stage. The monomer solution can be neutralized by mixing in the neutralizing agent. The hydrogel may be comminuted mechanically, for example by means of a meat grinder, in which case the neutralizing agent can be sprayed, sprinkled or poured on and then carefully mixed in. To this end, the gel mass obtained can be repeatedly ground in the meat grinder for homogenization. Neutralization of the monomer solution to the final degree of neutralization is preferred. The neutralized hydrogel is then dried with a belt or drum dryer until the residual moisture content is preferably below 15% by weight and especially below 10% by weight, the water content being determined by EDANA (European Disposables and Nonwovens Association) recommended test method No. 430.2-02 "Moisture content". If desired, drying can also be carried out using a fluidized bed dryer or a heated plowshare mixer. To obtain particularly white products, it is advantageous to dry this gel while ensuring rapid removal of the evaporating water. To this end, the dryer temperature must be optimized, the air feed and removal has to be controlled, and sufficient venting must be ensured in each case. The higher the solids context of the gel, the simpler the drying, by its nature, and the whiter the product. The solids content of the gel before the drying is therefore preferably between 30% and 80% by weight. It is particularly advantageous to vent the dryer with nitrogen or another nonoxidizing inert gas. If desired, however, it is possible simply just to lower the partial pressure of the oxygen during the drying in order to prevent oxidative yellowing processes. In general, though, adequate venting and removal of the water vapor also still lead to an acceptable product. A very short drying time is generally advantageous with regard to color and product quality.

The dried hydrogel is preferably ground and sieved, useful grinding apparatus typically including roll mills, pin mills or swing mills. The particle size of the sieved, dry hydrogel is preferably below 1000 μm, more preferably below 900 μm and most preferably below 800 μm, and preferably above 100 μm, more preferably above 150 μm and most preferably above 200 μm.

Very particular preference is given to a particle size (sieve cut) of from 106 to 850 μm. The particle size is determined according to EDANA (European Disposables and Nonwovens Association) recommended test method No. 420.2-02 "Particle size distribution".

The base polymers are then preferably surface postcrosslinked. Postcrosslinkers suitable for this purpose are compounds comprising two or more groups capable of forming covalent bonds with the carboxylate groups of the hydrogel. Suitable compounds are, for example, alkoxysilyl compounds, polyaziridines, polyamines, polyamidoamines, di- or polyglycidyl compounds, as described in EP-A 0 083 022, EP-A 0 543 303 and EP-A 0 937 736, di- or polyfunctional alcohols, as described in DE-C 33 14 019, DE-C 35 23 617 and EP-A 0 450 922, or β-hydroxyalkylamides, as described in DE-A 102 04 938 and U.S. Pat. No. 6,239,230.

In addition, DE-A 40 20 780 describes cyclic carbonates, DE-A 198 07 502 2-oxazolidone and its derivatives, such as 2-hydroxyethyl-2-oxazolidone, DE-A 198 07 992 bis- and poly-2-oxazolidinones, DE-A 198 54 573 2-oxotetrahydro-1,3-oxazine and its derivatives, DE-A 198 54 574 N-acyl-2-oxazolidones, DE-A 102 04 937 cyclic ureas, DE-A 103 34 584 bicyclic amide acetals, EP-A 1 199 327 oxetanes and cyclic ureas and WO 03/031482 morpholine-2,3-dione and its derivatives, as suitable surface postcrosslinkers.

The postcrosslinking is typically carried out in such a way that a solution of the surface postcrosslinker is sprayed onto the hydrogel or onto the dry base polymer powder. After the spraying, the polymer powder is dried thermally, and the crosslinking reaction may take place either before or during drying.

The spraying with a solution of the crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Suitable mixers are, for example, Lödige® mixers, Bepex® mixers, Nauta® mixers, Processall® mixers and Schugi® mixers.

The thermal drying is preferably carried out in contact dryers, more preferably shovel dryers and most preferably disk dryers. Suitable dryers are, for example, Bepex® dryers and Nara® dryers. It is also possible to use fluidized bed dryers.

The drying can be effected in the mixer itself, by heating the jacket or blowing in warm air. It is equally possible to use a downstream dryer, for example a tray dryer, a rotary tube oven or a heatable screw. It is also possible, for example, to utilize an azeotropic distillation as a drying process.

Preferred drying temperatures are in the range from 50 to 250° C., preferably in the range from 50 to 200° C. and more preferably in the range from 50 to 150° C. The preferred residence time at this temperature in the reaction mixer or dryer is below 30 minutes and more preferably below 10 minutes.

The present invention further provides an apparatus for carrying out the continuous neutralization process according to the invention, comprising
i) a ring line R,
ii) at least one first inlet $Z_1$ into the ring line R,
iii) at least one second inlet $Z_2$ into the ring line R,
iv) at least one heat exchanger W in the ring line R, the heat exchanger W being disposed beyond the inlets $Z_1$ and $Z_2$ in flow direction,
v) at least one outlet A from the ring line R, the outlet A being disposed beyond the heat exchanger W in flow direction,
vi) a pump P and
vii) if desired, a vessel B between the heat exchanger W and the outlet A,
where at least one first inlet $Z_1$ means that reactant 1, for example sodium hydroxide solution, is supplied via one or more inlets $Z_1$, and at least one second inlet $Z_2$ means that reactant 2, for example acrylic acid, is supplied via one or more inlets $Z_2$.

The ring line cross section Q is preferably from 20 to 2000 $cm^2$, more preferably from 80 to 700 $cm^2$, most preferably from 200 to 500 $cm^2$. The ring line R preferably has a circular cross section.

The totality of the inlets $Z_1$ has a cross section of preferably from 1.5 to 100 $cm^2$, more preferably from 6 to 35 $cm^2$, most preferably from 15 to 25 $cm^2$. The inlets $Z_1$ preferably have a circular cross section.

The totality of the inlets $Z_2$ has a cross section of preferably from 1.5 to 100 $cm^2$, more preferably from 6 to 35 $cm^2$, most preferably from 15 to 25 $cm^2$. The inlets $Z_2$ preferably have a circular cross section.

The pump P has a delivery capacity of preferably from 1 to 1000 t/h, more preferably from 10 to 700 t/h, most preferably from 100 to 500 t/h.

The vessel B has a volume of preferably from 1 to 100 m³, more preferably from 10 to 100 m³, most preferably from 20 to 50 m³.

The inlets $Z_1$ and $Z_2$ are preferably arranged in succession, the inlets $Z_1$ preferably being before the inlets $Z_2$ in flow direction.

The distance between the inlets $Z_1$ and $Z_2$ is preferably from 10 to 500%, more preferably from 50 to 300%, most preferably from 80 to 200%, of the square root of the ring line cross section Q.

Preferably at least two inlets $Z_1$ and/or $Z_2$ are present, more preferably two, three, four, five or six inlets $Z_1$ and $Z_2$, the inlets $Z_1$ and $Z_2$ preferably being arranged such that they have a common axis (for two inlets $Z_1$ and $Z_2$) or form a symmetrical star (for at least three inlets $Z_1$ and $Z_2$) and the axis or star is at right angles to the flow direction of the neutralized solution (multiple addition points).

Particularly advantageously, two, three or four multiple addition points are arranged in succession.

For example, at least eight inlets $Z_1$ may be present, in which case four inlets $Z_1$ in each case open in a cross shape into the ring line R, the at least 2 groups of four inlets $Z_1$ being arranged in succession and offset relative to one another.

Moreover, at least one third inlet $Z_3$ may open into the ring line R, where at least one third inlet $Z_3$ means that reactant 3, for example water, is supplied via one or more inlets $Z_3$, and inlet $Z_3$ is before inlet $Z_1$ in flow direction and/or encloses inlet $Z_1$.

The distance between inlets $Z_3$ and $Z_1$ is preferably from 10 to 500%, more preferably from 50 to 300%, more preferably from 80 to 200%, of the square root of the ring line cross section Q.

The ring line R is preferably configured as a Venturi tube at least one inlet $Z_1$ to $Z_3$.

The inlets more preferably open into a common Venturi tube.

The apparatus is preferably free of dead spaces; preferred materials are stainless steels, for example materials No. 1.4541 and No. 1.4571 to DIN 17007.

The surfaces should have minimum roughness.

Dead spaces are sections of the apparatus in which the average residence time is increased in the course of operation as intended.

EXAMPLES

The peak temperature of the following examples was calculated with Fluent 6.0. The peak temperature is the highest temperature occurring in the system. The program can be purchased, for example, via Fluent Deutschland GmbH, Birkenweg 14a, D-64295 Darmstadt. Further suppliers can be found under www.fluent.com.

Examples 1 to 6

For Examples 1 to 6, an apparatus as described in FIG. 1 was assumed. For the calculation, the diameter of the ring line R was set at 20 cm, the diameter of the feeds $Z_1$ to $Z_3$ each at 5 cm, the mass flow rate in the ring line R before feed $Z_3$ at 349 t/h, the temperature of the mass flow rate in ring line R before feed $Z_3$ at 26° C., the distance between feed $Z_3$ and feed $Z_1$ at 20 cm, the distance between feed $Z_1$ and feed $Z_2$ at 20 cm, the mass flow rate of acrylic acid at 11.5 t/h, the mass flow rate of 50% by weight sodium hydroxide solution at 8.4 t/h and the mass flow rate of water at 5 t/h.

Examples 1 to 3 demonstrate the influence of the metering sequence.

In Examples 4 to 6, sodium hydroxide solution and water are premixed. In Examples 5 and 6, the calculation was additionally supplemented by cooling of the sodium hydroxide solution/water mixture to the temperature specified before entry into the ring line R.

The examples demonstrate how the peak temperature can be influenced via the metering sequence.

| | Feed | | | Temperature | | | Peak |
|---|---|---|---|---|---|---|---|
| Example | $Z_3$ | $Z_1$ | $Z_2$ | NaOH | $H_2O$ | AA | temperature |
| 1 | $H_2O$ | AA | NaOH | 23° C. | 23° C. | 23° C. | 64° C. |
| 2 | NaOH | $H_2O$ | AA | 23° C. | 23° C. | 23° C. | 47° C. |
| 3 | AA | $H_2O$ | NaOH | 23° C. | 23° C. | 23° C. | 64° C. |
| 4 | — | NaOH/$H_2O$ | AA | 23° C. | 23° C. | 23° C. | 43° C. |
| 5 | — | NaOH/$H_2O$ | AA | 23° C.*) | 23° C.*) | 15° C. | 38° C. |
| 6 | — | NaOH/$H_2O$ | AA | 15° C.*) | 15° C.*) | 15° C. | 35° C. |

NaOH: 50% by weight sodium hydroxide solution
$H_2O$: water
AA: acrylic acid
*)Temperature of the NaOH/$H_2O$ mixture

Examples 7 to 9

Examples 7 to 9 were calculated analogously to Examples 1 to 6.

For the calculation of Examples 7 to 9, it was assumed that an NaOH/$H_2O$ mixture and acrylic acid are metered into a common Venturi tube. The length of the Venturi tube was set at 93.2 cm, the Venturi tube narrowing to a diameter of 10 cm over a distance of 8.4 cm, retaining the diameter of 10 cm over a distance of 27.6 cm and widening again to a diameter of 20 cm over a distance of 57 cm. The distance of the feed $Z_1$ from the point where the Venturi tube has narrowed to 10 cm was assumed to be 5 cm, the distance of feed $Z_2$ from feed $Z_1$ to be 8 cm and the diameter of the two feeds $Z_1$ and $Z_2$ in each case to be 3.5 cm. The two feeds $Z_1$ and $Z_2$ in each case are arranged opposite one another, the connecting axis of the two feeds $Z_1$ being rotated by 90° relative to the connecting axis of the two feeds $Z_2$.

In Examples 7 to 9, the influence of the mass flow rate in the ring line R was additionally examined. In Examples 8 and 9, the mass flow rate in the ring line R was therefore reduced by 50% and 90% respectively in the calculation.

| Exam-ple | Mixing ratio | Feed $Z_1$ | $Z_2$ | Temperature NaOH/$H_2O$ | AA | Peak temperature |
|---|---|---|---|---|---|---|
| 7 | 1:10 | NaOH/$H_2O$ | AA | 15° C. | 15° C. | 27° C. |
| 8 | 1:5 | NaOH/$H_2O$ | AA | 15° C. | 15° C. | 46° C. |
| 9 | 1:1 | NaOH/$H_2O$ | AA | 15° C. | 15° C. | 69° C. |

The calculations also demonstrate the advantages of the Venturi tube over simple metering (comparison of Examples 6 and 7).

What is claimed is:

1. A neutralization process in which at least one ethylenically unsaturated carboxylic acid having a temperature from 0° C. to 40° C. is neutralized partly with a base, which comprises carrying out the neutralization continuously and a temperature of the neutralized solution being less than 70° C., wherein the neutralized solution is recycled partly into the neutralization.

2. The process according to claim 1, wherein the carboxylic acid and/or the base is diluted with water.

3. The process according to claim 1, wherein the neutralized solution is cooled.

4. The process according to claim 1, wherein between 25 and 95% of the neutralized solution is recycled.

5. The process according to claim 1, wherein the base is aqueous alkali.

6. The process according to claim 1, wherein the recycled neutralized solution, in the neutralization, is admixed successively with the base and the ethylenically unsaturated carboxylic acid.

7. The process according to claim 1, wherein the recycled neutralized solution, in the neutralization, is admixed successively with water, the base, and the ethylenically unsaturated carboxylic acid.

8. The process according to claim 5, wherein the ethylenically unsaturated carboxylic acid has a temperature of from 15 to 25° C. and/or the aqueous alkali has an alkali content of less than 25% by weight and a temperature of from 15 to 30° C. or the aqueous alkali has an alkali content of at least 25% by weight and a temperature of from 30 to 50° C. and/or, if used, the water has a temperature of from 15 to 30° C.

9. The process according to claim 1, wherein at least one metering point for the base, the ethylenically unsaturated carboxylic acid and, if used, the water is designed as a Venturi tube.

10. The process according to claim 5, wherein the aqueous alkali is a sodium hydroxide solution and/or the ethylenically unsaturated carboxylic acid is acrylic acid.

11. A process for preparing water-absorbing polymers, comprising a neutralization process according to claim 1.

12. A neutralization process in which at least one ethylenically unsaturated carboxylic acid having a temperature from 0° C. to 40° C. is neutralized partly with a base, which comprises carrying out the neutralization continuously and a temperature of the neutralized solution being less than 50° C., wherein the neutralized solution is recycled partly into the neutralization, and the recycled neutralized solution, in the neutralization, is admixed successively with the base and the ethylenically unsaturated carboxylic acid.

13. The process according to claim 12, wherein between 25 and 95% of the neutralized solution is recycled.

14. The process according to claim 12, wherein at least one metering point for the base, the ethylenically unsaturated carboxylic acid and, if used, the water is designed as a Venturi tube.

15. A process for preparing water-absorbing polymers, comprising a neutralization process according to claim 12.

* * * * *